(12) United States Patent
Cook et al.

(10) Patent No.: US 9,579,135 B2
(45) Date of Patent: Feb. 28, 2017

(54) PLATE AND SCREW APPARATUS AND METHODS THEREOF

(71) Applicant: Fellowship of Orthopaedic Researchers, LLC, Metairie, LA (US)

(72) Inventors: Stephen D. Cook, New Orleans, LA (US); Shoib Bajaj, Austin, TX (US)

(73) Assignee: Fellowship of Orthopaedic Researchers, LLC, Metairie, LA (US)

( * ) Notice: Subject to any disclaimer, the term of this patent is extended or adjusted under 35 U.S.C. 154(b) by 243 days.

(21) Appl. No.: 13/707,250

(22) Filed: Dec. 6, 2012

(65) Prior Publication Data

US 2013/0165980 A1    Jun. 27, 2013

Related U.S. Application Data

(60) Provisional application No. 61/579,630, filed on Dec. 22, 2011.

(51) Int. Cl.
*A61B 17/80* (2006.01)

(52) U.S. Cl.
CPC ...... *A61B 17/8033* (2013.01); *A61B 17/8047* (2013.01)

(58) Field of Classification Search
CPC .................. A61B 17/8033; A61B 17/8047

USPC ..... 606/70, 71, 246–279, 280–299, 300–331
See application file for complete search history.

(56) References Cited

U.S. PATENT DOCUMENTS

| | | | | |
|---|---|---|---|---|
| 5,735,853 A | * | 4/1998 | Olerud | A61B 17/7059 606/289 |
| 6,641,583 B2 | * | 11/2003 | Shluzas | A61B 17/7004 606/252 |
| 7,857,836 B2 | * | 12/2010 | Huebner | A61B 17/8047 606/280 |
| 2003/0078583 A1 | * | 4/2003 | Biedermann | A61B 17/8047 606/290 |
| 2008/0132960 A1 | * | 6/2008 | Weaver | A61B 17/8057 606/308 |
| 2010/0228252 A1 | * | 9/2010 | Courtney | A61B 17/7059 606/70 |

* cited by examiner

*Primary Examiner* — Christopher Beccia
(74) *Attorney, Agent, or Firm* — Frommer Lawrence & Haug; Stephen J. Lieb; Russell A. Garman

(57) ABSTRACT

This disclosure provides a plate having at least a first aperture and a second aperture, and at least a first annulus adaptable to be disposed within the first aperture and at least a second annulus adaptable to be disposed within the second aperture. Further provided is at least a first screw adaptable to be disposed within the first annulus and at least a second screw adaptable to be disposed within the second annulus, wherein the first and second screws are each engageable with its respective first and second annulus.

13 Claims, 5 Drawing Sheets

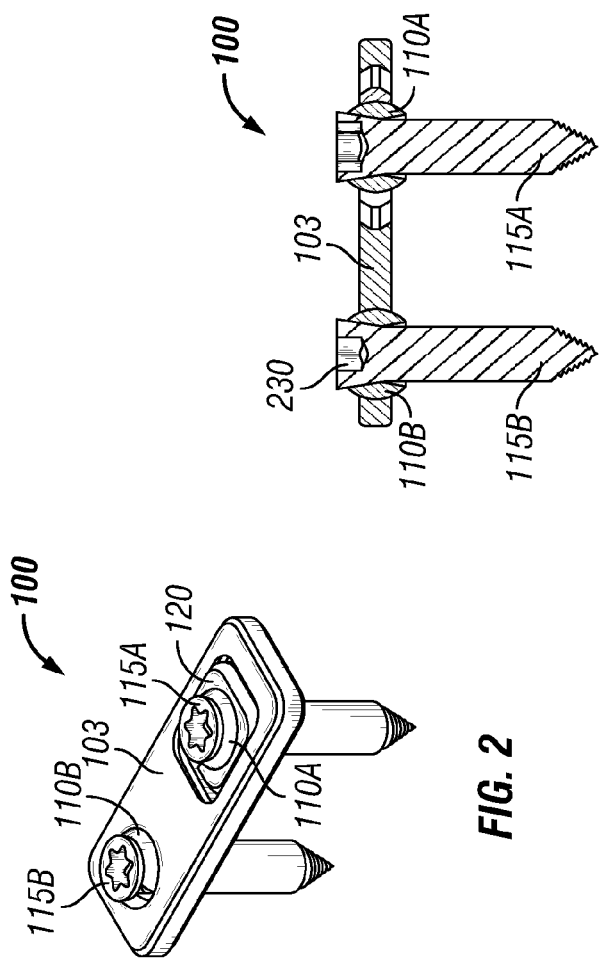
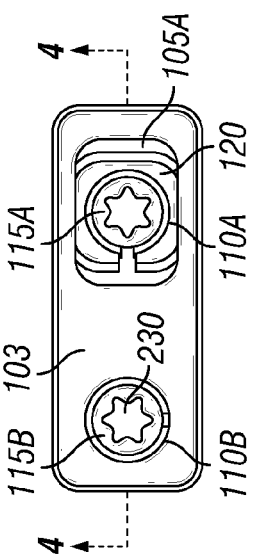
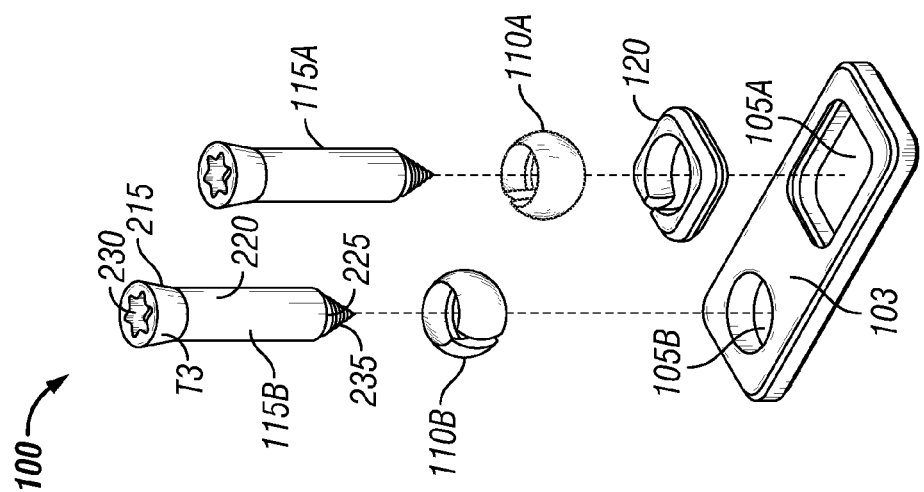

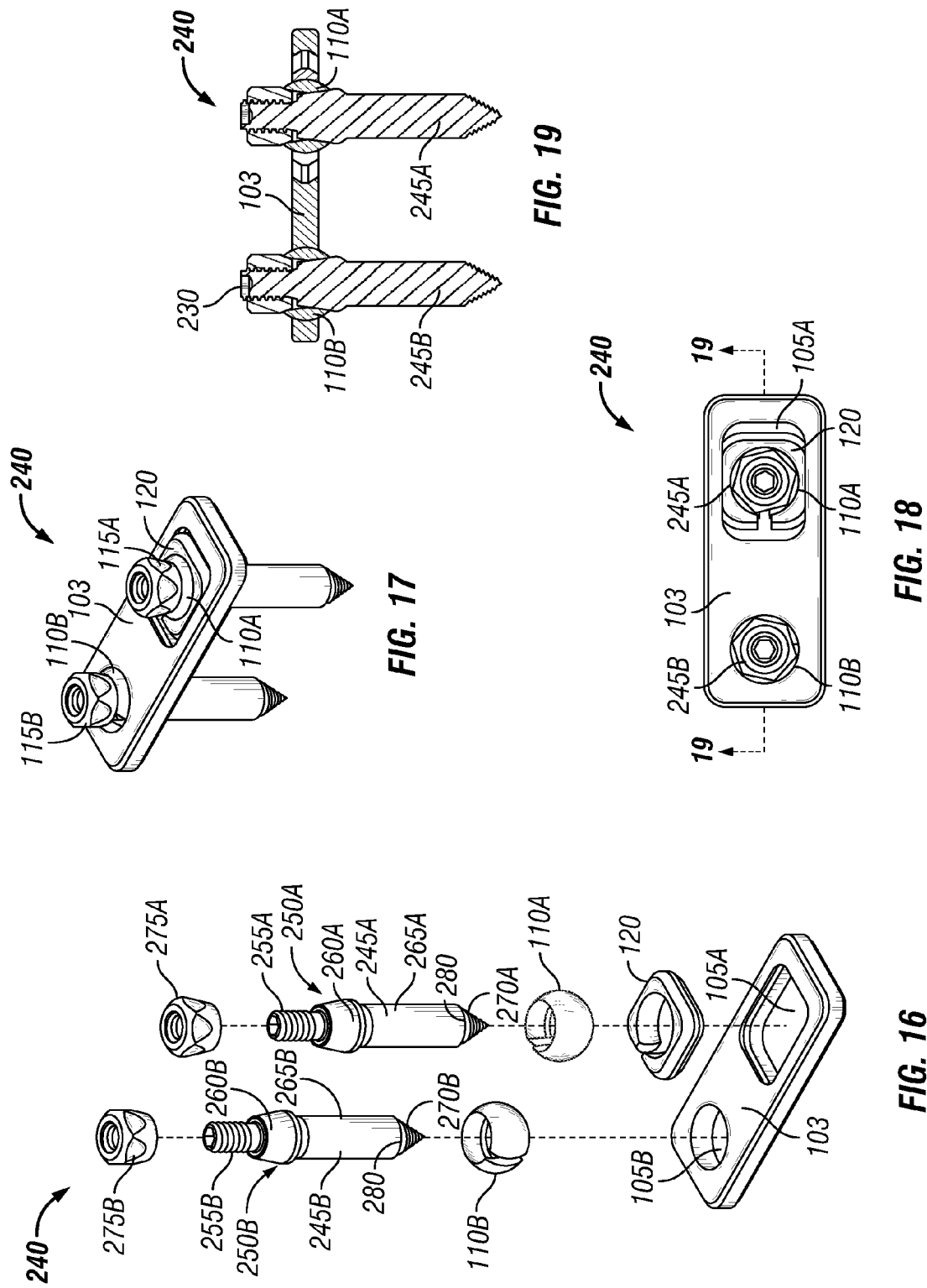

PLATE AND SCREW APPARATUS AND METHODS THEREOF

CROSS-REFERENCE TO RELATED APPLICATIONS

This Non-Provisional U.S. patent application claims the benefit of and priority to the earlier-filed U.S. Provisional Patent Application Ser. No. 61/579,630, filed on Dec. 22, 2011, the entire contents of which is hereby incorporated by reference in full.

BACKGROUND OF THE INVENTION

The bones of vertebrates (including mammals such as humans) can break or fracture, due to injury, heredity, or combinations thereof. Prior apparatuses and methods for fixation or fusion of bones and joints to promote healing and/or reduce future injury are generally known.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure.

FIG. 1 is an exploded view of an illustrative plate and screw apparatus of the present disclosure;

FIG. 2 is a perspective view an illustrative plate and screw apparatus of the present disclosure;

FIG. 3 is a top down view of the illustrative plate and screw apparatus of the FIG. 2;

FIG. 4 is a cross-sectional view of the illustrative plate and screw apparatus of FIGS. 2 and 3 taken along cut line 4-4 of FIG. 3;

FIG. 16 is an exploded view of an alternative illustrative plate and screw apparatus of the present disclosure;

FIG. 17 is a perspective view an illustrative alternative plate and screw apparatus of the present disclosure;

FIG. 18 is a top down view of the alternative illustrative plate and screw apparatus of the FIG. 17;

FIG. 19 is a cross-sectional view of the illustrative plate and screw apparatus of FIGS. 17 and 18 taken along cut line 19-19 of FIG. 18;

DETAILED DESCRIPTION OF THE INVENTION

Figure 5:
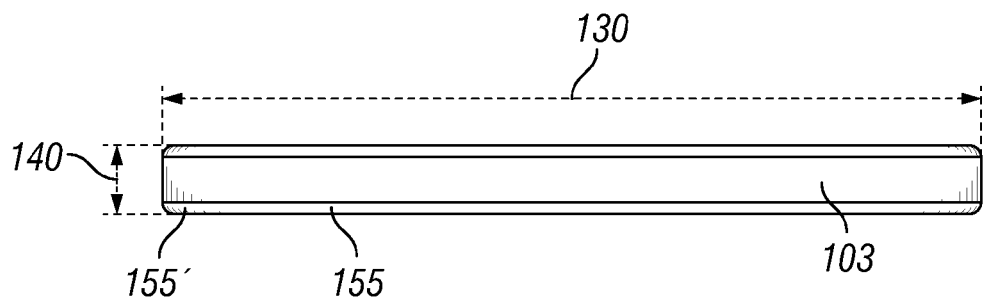
FIG. 5 is a side view of an illustrative plate of the present disclosure.
Figure 6:
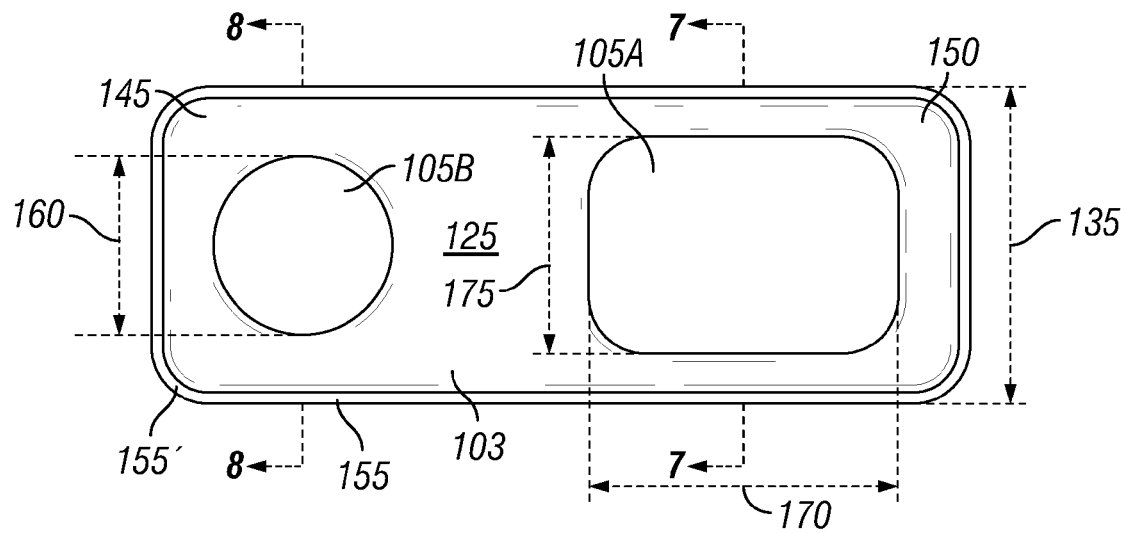
FIG. 6 is a top-down view of the illustrative plate of FIG. 5.
Figure 7:
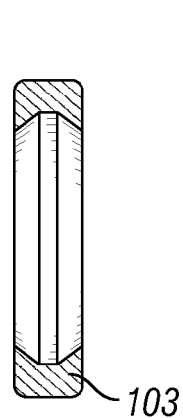
FIG. 7 is a cross-sectional view of the illustrative plate of FIGS. 5 and 6 taken along cut line 7-7 of FIG. 6.
Figure 8:
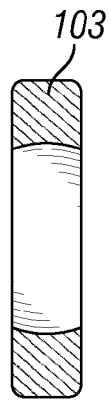
FIG. 8 is a cross-sectional view of the illustrative plate of FIGS. 5 and 6 taken along cut line 8-8 of FIG. 6.
Figure 9:
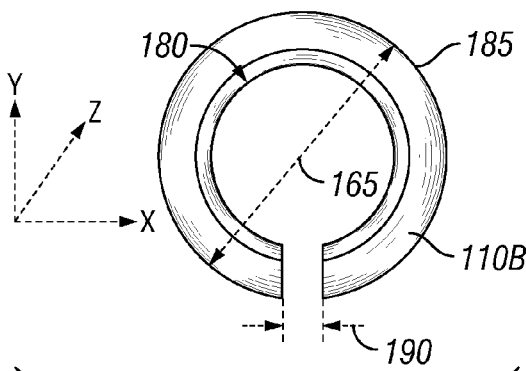
FIG. 9 is a top-down view of an illustrative annulus of the present disclosure.
Figure 10:
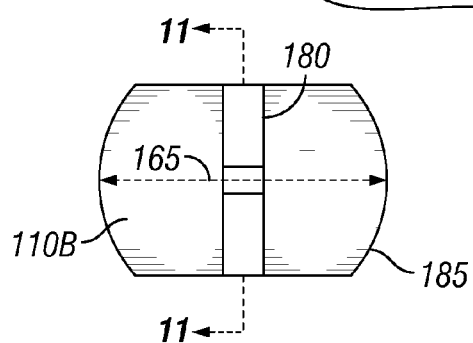
FIG. 10 is a side-view of the illustrative annulus of FIG. 9.
Figure 11:
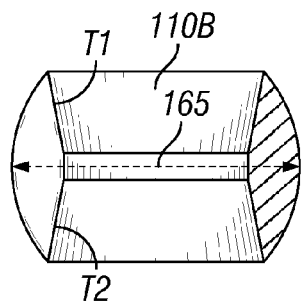
FIG. 11 is a cross-sectional view of the illustrative annulus of FIGS. 9 and 10 taken along cut line 11-11 of FIG. 10.

Detailed embodiments of the present plate and screw apparatus, and methods thereof are disclosed herein; however, it is to be understood that the disclosed embodiments are merely illustrative of the plate and screw apparatus and methods that may be embodied in various forms. In addition, each of the examples given in connection with the various embodiments of the systems and methods are intended to be illustrative, and not restrictive. Further, the drawing figures are not necessarily to scale, and some features may be exaggerated to show details of particular components. In addition, any measurements, specifications and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the present apparatus or system, and methods thereof.

With reference to FIGS. 1, 2, 3, and 4, an embodiment of a plate and screw apparatus 100 is provided. The plate and screw apparatus 100 may include a plate 103 having at least two bores 105A, 105B. Each respective bore 105A, 105B may receive or otherwise be engaged with an annulus, or collar, 110A, 110B. Each respective annulus, or collar, 110A, 110B may receive or be engaged with a screw 115A, 115B. The bores 105A, 105B may independently have any horizontal-cross-sectional shape including, generally trapezoidal, circular, rectangular, triangular, and the like. In the embodiments of FIGS. 1, 2, 3, and 4, the bores 105A and 105B have generally trapezoidal and circular horizontal-cross-sectional shapes, respectively; however, in alterative embodiments, the bores 105A and 105B may have the same horizontal-cross-sectional shape (such as for example, both generally trapezoidal or both generally circular). In an embodiment, at least one bore 105A may have a trapezoidal cross-sectional shape and the bore 105A may receive or otherwise be engaged with an annulus retainer, or slide, 120. In this embodiment, the annulus retainer, or slide, 120 may receive or otherwise be engaged with the annulus, or collar, 110A, which may receive or be engaged with the screw 115A.

Figure 12:
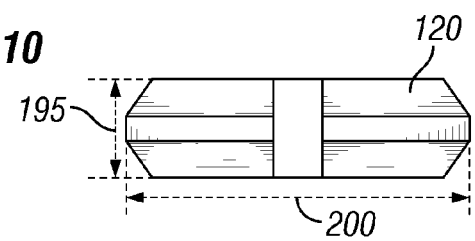
FIG. 12 is a side view of an illustrative slide of the present disclosure.
Figure 13:
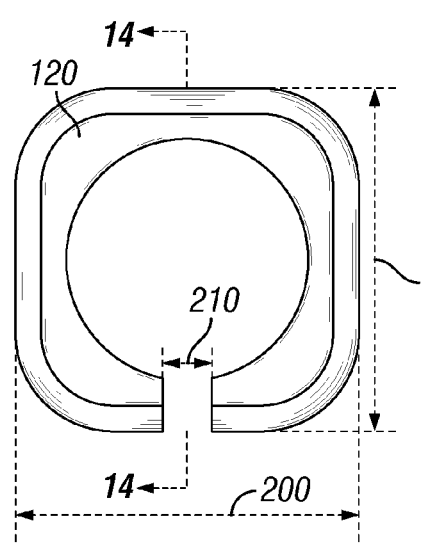
FIG. 13 is a top-down view of the illustrative slide of FIG. 12.
Figure 14:
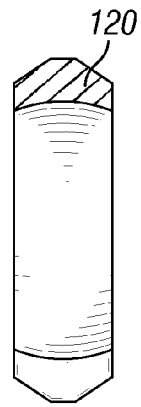
FIG. 14 is a cross-sectional view of the illustrative slide of FIGS. 12 and 13 taken along cut line 14-14 of FIG. 13.
Figure 15:
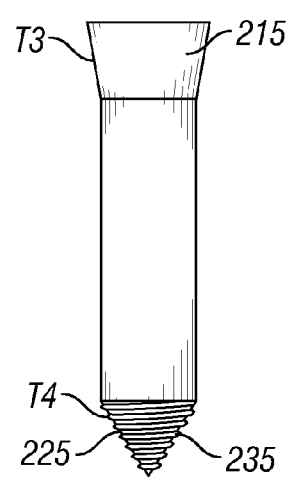
FIG. 15 is a side view of an illustrative screw of the present disclosure.
Figure 23:
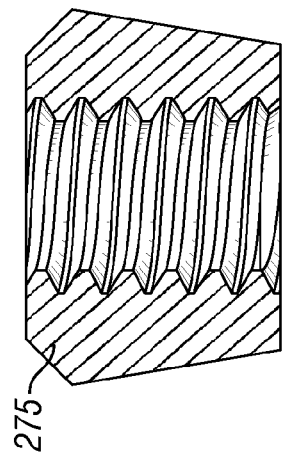
FIG. 23 is a cross-sectional view of the illustrative embodiment of the nut engaged with the alternative screw of FIGS. 21 and 22 taken along cut line 23-23 of FIG. 22.
Figure 21:
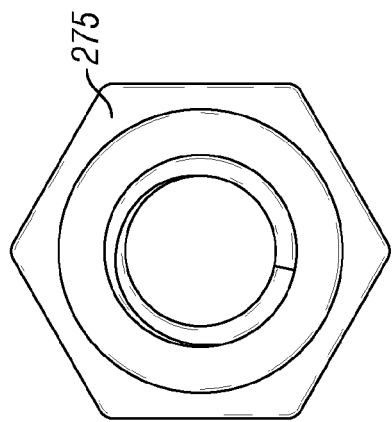
FIG. 21 is a top down view of an illustrative embodiment of a nut engaged with an alternative screw of the present disclosure.
Figure 22:
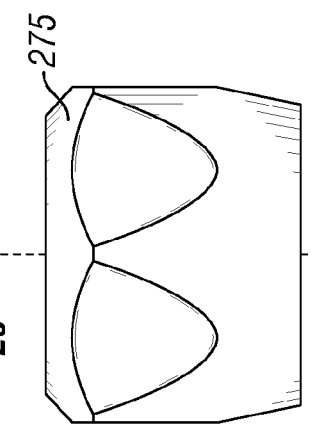
FIG. 22 is a side view of the illustrative embodiment of the nut engaged with the alternative screw of FIG. 21.
Figure 20:
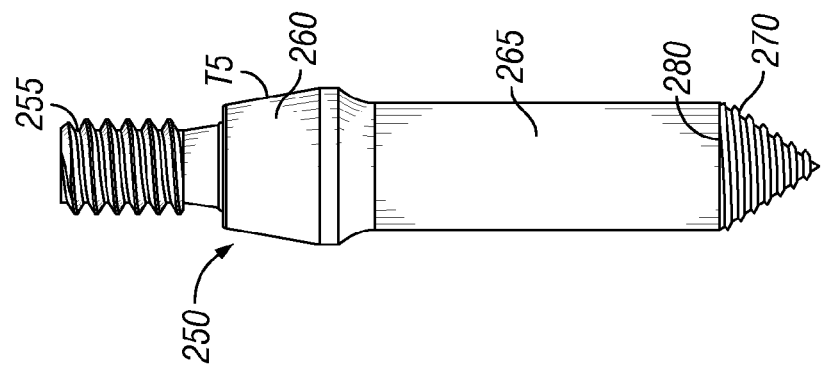
FIG. 20 is a side view of an illustrative alternative screw of the present disclosure.

In an embodiment and with reference to FIGS. 5, 6, 7, and 8, the plate 103 may be any size and shape suitable to bridge a bone or joint break, fracture, dislocation, or joint fusion. In an embodiment, the plate 103 may have a generally trapezoidal horizontal-cross-section 125 with a length 130 ranging from about 1 to about 6 inches; alternatively from about 1 to about 3 inches; alternatively from about 0.5 to about 1.5 inches; alternatively about 2 inches, a width 135 ranging from about 0.5 to about 1.5 inches; alternatively about 0.75 inch, and a depth, or height, 140 ranging from about 0.1 to about 0.5 inches; alternatively about 0.25 inches. The ends 145, 150 of the plate 100 may have a profile ranging from curved to rectangular, including generally arced and generally semi-circular. In an embodiment, the ends 145, 150 of the plate 103 may have a profile of a general outside arc ranging from about 0.1 inches to about 0.75 inches. The plate 103 may have a plurality of edges 155, 155' each having a fillet radii independently ranging from about 0.01 to about 0.125. The bore 105B, which may or may not be tapered along a vertical axis, may have a minimum bore diameter 160, which may range from about 0.1 inches to about 0.75 inches and alternatively may be about 0.2 inches or about 0.25 inches. In other embodiments, the minimum bore diameter 160 may be less than or equal the maximum annulus diameter 165 (described herein with respect to FIGS. 1, 9, 10, and 11) of the annulus 110B. In an embodiment, the trapezoidal bore 105A, which may or may not be tapered along a vertical axis, may have a maximum trapezoidal bore length 170 that is greater than or equal the length of the slide 120 (described herein with respect to FIGS. 12, 13, and 14) and a maximum trapezoidal bore width 175 that is less than or equal to the width of the slide 120. In various embodiments, the inner surface of the bores 105A, 105B and the outer surface of annulus 110A, 110B may each be machined to a heavy texture (for example texturing by grid blasting) to enhance or otherwise improve the friction fit between component elements/parts and prevent (or reduce) rotation of the component elements/parts about themselves. The surface roughness RMS of at least a portion of the bores 105A and 105B may range from about 25 microinches to about 300 microinches (as tested by ASTM D7127-05).

In an embodiment and with reference to FIGS. 1, 9, 10, and 11, the annulus 110A, 110B may have an interior surface 180 and an exterior surface 185. The interior surface 180 of the annulus 110A may have a taper, T1, across its vertical-cross-sectional face. In an alternative embodiment (shown), the interior surface 180 of the annulus 110A may have two tapers, T1 and T2, across its vertical-cross-sectional face, such that it may be inserted into the bore 105A or slide 120 without regard to an "up" or "down" orientation. In other words, in an embodiment, the interior surface 180 may be symmetric about an "x" or horizontal axis, and it does not matter which "end" is inserted into the bore 105 or slide 120. In an embodiment, the tapers, T1 and T2, may be of the same, similar, or different angles, which may independently range from about 1 degree from vertical to about 20 degrees from vertical; alternatively from about 1 degree to about 10 degrees. Preferably, the annulus 110A, 110B has a height ranging from about 0.1 inches to about 0.5 inches, and alternatively about 0.3 inches, with each taper being separated by a vertical space, S, ranging from about 0.02 inches to about 0.4 inches. The exterior surface 185 of the annulus 110 may form a general semi-circle. In an embodiment, the radius of the semi-circular exterior surface 185 may range from about 0.1 inches to about 0.4 inches, and alternatively be about 0.2 inches. In an embodiment, a force placed along the interior surface 180 of the annulus 110, may expand the annulus 110 radially. In an embodiment, the annulus 110 may have an annulus gap 190, which may facilitate the expansion of the annulus 110 without breaking or fracturing the annulus 110. In an embodiment, the annulus gap 190 may have a length ranging from about 0.02 inches to about 0.1 inches, and alternatively be about 0.06 inches. The surface roughness RMS of at least a portion of the annulus 110A, 110B may range from about 25 microinches to about 300 microinches (as tested by ASTM D7127-05).

In an embodiment and with reference to FIGS. 1, 12, 13, and 14, the slide 120 may be any size and shape suitable for engagement with a respective bore of the plate 103. In various embodiments, the slide 120 may have a generally trapezoidal horizontal-cross-sectional shape that is suitable for engagement with the generally trapezoidal bore 105B of the plate 103. In an embodiment, suitable engagement of the slide 120 within the bore 105B is engagement such that the slide 120 fits snugly within the bore 105B and at the same time can be moved or slid in at least one direction within the bore 105B. For example, the slide 120 may be suitably engaged within the bore 105B when a maximum width of the slide 120 is approximately equal to a maximum width of the bore 105B and the length of the slide 120 is less than the length of the bore 105B. In an embodiment, the slide 120 may be slid in at least one direction (alternatively two or three) within the rectangular bore before it is fit into place.

In various embodiments herein, the slide 120 may have a maximum slide depth 195 ranging from about 0.1 to about 0.5 inches; alternatively about 0.25 inches; a maximum slide length 200 ranging from about 0.25 to about 1 inch and alternatively about 0.75 inches; and a maximum slide width 205 of ranging from about ⅛ inch to about 0.75 inches and alternatively about 0.5 inches. In various embodiments, the slide 120 may have a slide bore 210, optionally through which the screw 115 may be receive. The radius of the slide bore 120 may range from about 0.1 inches to about 0.75 inches and alternatively may be about 0.2 inches or about 0.25 inches. The slide 120 may have a slide gap 210, which may facilitate the expansion of the slide 120 without breaking or fracturing the slide 120. The slide 120 (like the annulus 110A, 110B) may expand or move out radially when the screw 115 is engaged therewith (or otherwise driven down) to "lock" the screw 115 in place within the plate 103 by a (preferably snug or tight) friction fit. In an embodiment, the slide gap 210 may have a length ranging from about 0.02 inches to about 0.1 inches, and alternatively be about 0.06 inches. The surface roughness RMS of at least a portion of the slide 120 may range from about 25 microinches to about 300 microinches (as tested by ASTM D7127-05).

In an embodiment and with reference to FIGS. 1, 2, 4, and 15, the screw 115 may have a head portion 215, a body portion 220, and a tip portion 225. The head portion 215 may include a tapered circumference, T3, (otherwise called a bugle portion, a bugle head, a flat head, or a countersunk head). In an embodiment, the tapered head circumference, T3, may range from about 1 degrees from vertical to about 20 degrees from vertical and alternatively from about 1 degree to about 10 degrees. The head portion 215 may have a truncated conical cross section. In an embodiment, T1, T2, and T3 have approximately equal degrees of tapers. The head portion 215 may further include recesses 230 (shown in FIGS. 1 and 3) which may be of any shape, including a torx, which is sufficient to receive a screw driver (not shown). In an embodiment, the head portion 215 may have a height ranging from about 0.1 inches to about 0.4 inches, and preferably 0.2 inches. In an embodiment, the head portion 215 may have a maximum head diameter, which may range from about 0.1 inches to about 0.5 inches, at the head portion's 215 upper most circumference and tapers along T3 down to lesser diameters until it is about the same, or the same, diameter as the body portion 220.

The body portion 220 of the screw 115 may be of any cross section, including generally cylindrical and generally tapered or truncated conical. In an embodiment, the body portion 220 of the screw 115 may have a length ranging from about 0.5 inches to about 3 inches, alternatively from 1 inch to about 2 inches. In an embodiment, the body portion 220 of the screw 115 may have a maximum diameter ranging from about 0.1 inches to about 0.5 inches, and preferably about 0.25 inches. In various embodiments where the body portion 220 of the screw 115 is a generally truncated cone, the taper angle (not shown) may range from about 1 degree to about 10 degrees. In various embodiments, at least a portion of the body portion 220 may be of a generally truncated cone may include threads (not shown, but generally equivalent to the threads (235 of the tip portion 225 described below).

In still a further embodiment (not shown) the body portion 220 may include a combination of a generally cylindrical portion blended into a generally truncated conical portion. In this embodiment, the generally cylindrical portion of the body portion 220 may be preferably blended into the head portion 215 and may have a length ranging from about 0.1 inches to about 0.5 inches. In the embodiment having a combination of a generally cylindrical portion blended into a generally truncated conical portion, the generally truncated conical portion may be preferably blended into the tip portion 225.

In an embodiment, the tip portion 225 of the screw 115 may include a plurality of threads 235, which may optionally be suitable for biting into or otherwise engaging the bone of a patient (not shown). In an embodiment, the tip portion 225 of the screw 115 may have a length ranging from about 0.2 inches to about 0.4 inches. In an embodiment, the tip portion 225 of the screw 115 may have a maximum diameter ranging from about 0.1 inches to about 0.5 inches, and preferably about 0.25 inches. In various embodiments, the tip portion 225 may taper down along a taper T4 that may have an angle ranging from 15 degrees to about 45 degrees and alternatively about 30 degrees. In various embodiments, the terminal end of the tip portion 225 may have a diameter ranging from about a sharp point to about 0.2 inches.

In an embodiment, the screw 115 may be inserted into the annulus 110, which has been placed inside either the bore 105 or the slide 120. The screw 115 may be driven down (by a screw driver—not shown) such that at least its threaded tip portion 225 engages a material (such as a bone of a patient). In this manner, the screw head portion 215 may place a force along the interior surface 110A of the annulus 110 and cause it to expand (or move) out radially and against the sides of the bore 105 or slide 120, which may preferably "lock" the screw 215 in place within the plate 103 by a (preferably snug or tight) friction fit.

With reference to FIGS. 16 to 23, an alternative plate and screw apparatus 240 is provided. The alternative plate and screw apparatus 240 may include a plate 103 having bores 105A and 105B, annuluses 110A, 110B, at least one optional slide 120, and an alternative screw 245 having a head portion 250 having a threaded head portion 255 and a tapered head portion 260, a body portion 265, a tip portion 270, and a threaded nut 275. In the interest of brevity and ease of readability, Applicant refers the reader to the description herein of the plate 103, annulus 110, and slide 120 provided with respect to the screw 115 and elects, without prejudice, not to repeat the description with respect to the alternative plate and screw apparatus 240. Applicant respectfully asserts that one of ordinary skill will recognize modifications and adjustments (such as changes to the dimensions) of those component elements in view of the differences between the screw 115 and the alternative screw 245 as described herein.

The head portion 250 may include a threaded head portion 255 and a taper head portion 260 having a tapered circumference, T5. In an embodiment, the threaded head portion 255 may engage or otherwise be screwed into the threaded nut 275, which may have threads that are reciprocal with the threads of the threaded head portion. The tapered head portion 260 having a tapered circumference, T5, may range from about 1 degrees from vertical to about 20 degrees from vertical and alternatively from about 1 degree to about 10 degrees. The threaded head portion 255 may have a cylindrical cross section, which may flare, taper, or otherwise blend into the tapered head portion 260, which may have a truncated conical cross section. In an embodiment, T1, T2, and T5 have approximately equal degrees of tapers. The threaded nut 275 may include internal threads and a bore such that it may engage, receive, and otherwise be screwed onto, the threaded head portion 255. An illustrative embodiment of an engagement of the threaded nut 275 and threaded head portion 255 is provided in FIG. 23. In an embodiment, the head portion 250 may have a height ranging from about 0.1 inches to about 0.75 inches, and optionally 0.5 inches. The threaded head portion 255 may have a height ranging from about 0.1 inches to about 0.2 inches, and optionally about 0.25 inches. The tapered head portion 260 may have a height ranging from about 0.1 inches to about 0.4 inches. The tapered head portion 260 may blend or taper into the body portion 265.

The body portion 265 of the screw 245 may be of any cross section, including generally cylindrical and generally tapered or truncated conical. In an embodiment, the body portion 265 of the screw 245 may have a length ranging from about 0.5 inches to about 3 inches, alternatively from 1 inch to about 2 inches. In an embodiment, the body portion 265 of the screw 245 may have a maximum diameter ranging from about 0.1 inches to about 0.5 inches, and preferably about 0.25 inches. In various embodiments where the body portion 265 of the screw 245 is a generally truncated cone, the taper angle (not shown) may range from about 1 degree to about 10 degrees. In various embodiments, at least a portion of the body portion 265 may be of a generally truncated cone may include threads (not shown, but generally equivalent to the threads (135 of the tip portion 225 described above).

In still a further embodiment (not shown) the body portion 265 may include a combination of a generally cylindrical portion blended into a generally truncated conical portion. In this embodiment, the generally cylindrical portion of the body portion 265 may be preferably blended into the tapered head portion 260 and may have a length ranging from about 0.1 inches to about 0.5 inches. In the embodiment having a combination of a generally cylindrical portion blended into a generally truncated conical portion, the generally truncated conical portion may be preferably blended into the tip portion 270.

In an embodiment, the tip portion 270 of the screw 245 may include a plurality of threads 280, which may optionally be suitable for biting into or otherwise engaging the bone of a patient (not shown). In an embodiment, the tip portion 270 of the screw 245 may have a length ranging from about 0.2 inches to about 0.4 inches. In an embodiment, the tip portion 270 of the screw 245 may have a maximum diameter ranging from about 0.1 inches to about 0.5 inches, and preferably about 0.25 inches. In various embodiments, the tip portion 270 may taper down along a taper T6 that may have an angle ranging from 15 degrees to about 45 degrees and alternatively about 30 degrees. In various embodiments, the terminal end of the tip portion 270 may have a diameter ranging from about a sharp point to about 0.2 inches.

In an embodiment, the screw 245 may be inserted into the annulus 110, which has been placed inside either the bore 105 or the slide 120. The nut 275 may be aligned with the threaded head portion screw 255 and the nut may be driven down (by a wrench or other such tool—not shown) such that at least its threaded tip portion 270 engages a material (such as a bone of a patient). In this manner, at least a portion of the nut 275 (which may optionally be tapered or otherwise include tapered portions) and/or the tapered head portion 260 may place a force along the interior surface 110A of the annulus 110 and cause it to expand (or move) out radially and against the sides of the bore 105 or slide 120, which may preferably "lock" the screw 245 in place within the plate 103 by a (preferably snug or tight) friction fit.

Further embodiments may be readily understood with reference to the remainder of the drawing figures and schematics included herein.

In an embodiment, the plates and screws of the present disclosure may be fabricated from various orthopaedic biomaterials including stainless steels, cobalt chromium alloys, and titanium and its alloys. The plate may further be fabricated from various polymer materials such as polyethyletherketone (PEEK) and/or combinations of polymers and metals such as PPEK plates with titanium alloy spherical and slide inserts placed with titanium alloy screws.

In still further embodiments, the screws may be coated with a ceramic material such as hydroxyapatite which may have the benefit of a biologically more favorable surface, release of calcium and phosphate to the surrounding tissues due to slow dissolution. The release of these materials may aid in the biological fusion process. In addition, ceramic coatings may seal off the metal and reduce ion release and corrosion. Still other coatings such as titanium nitrides and chromium carbides may be used for better corrosion protection and reduction of metal ion release.

Without wishing to be bound by the theory, Applicant believes that the present apparatus allows for enhanced flexibility in the surgical placement of screws in various anatomical positions, and multiple orientations. For example, and without wishing to be bound by the theory, Applicant believes that the plate of the present disclosure may accept the screw of the present disclosure at various angles throughout a 360 degree circumference. Thus, in an embodiment, the plate of the disclosure may bridge a bone fracture or break or a joint fracture, break, or dislocation. A first screw may be inserted into the bone on one side of the bone fracture or break (or joint fracture, break, or dislocation) and a second screw may be inserted into bone on another side of the bone fracture or break (or joint fracture, break, or dislocation). The plate may then be screwed down and may keep the fractured or broken bone or joint in a general position/orientation to facilitate healing. In an embodiment, the plate and screw apparatus of the present disclosure may be placed across a sacroiliac joint that has been fractured, broken, or otherwise dislocated to facilitate healing or otherwise reduce risk of future/further injury.

What is claimed is:

1. An apparatus comprising:
   (a) a plate having at least a first aperture and a second aperture;
   (b) a rectangular slide having an external surface that is configured to engage with at least the first aperture, the first aperture comprising a lip for receiving the rectangular slide such that the rectangular slide cannot be removed from the first aperture, wherein the rectangular slide comprises a bore and a slide gap;
   (c) at least a first annulus adaptable to be disposed within the bore of the rectangular slide and at least a second annulus adaptable to be disposed within the second aperture,
      wherein the first and second annuluses each have an internal and an external surface, the internal surface of the first and second annuluses each has a symmetric annular taper along respective vertical cross sections; and the external surface of one or both of the first and second annuluses forms a general semi-circle along its vertical cross section; and
   (d) at least a first screw adaptable to be disposed within the first annulus and at least a second screw adaptable to be disposed within the second annulus,
      wherein the first and second screws each have a head portion, a body portion, and an end portion.

2. The apparatus of claim 1, wherein the head portion of the first and second screws each has a respective screw-head taper that is engageable with its respective symmetric annular taper.

3. The apparatus of claim 1, wherein the end portion of each screw is threaded.

4. The apparatus of claim 3, wherein the threaded end portion of the first screw is configured to be engaged with a sacrum of a patient and the second screw is configured to be engaged with an ilium of a pelvis of the patient, and the plate of the apparatus bridges a sacroiliac joint of the patient.

5. The apparatus of claim 2, wherein the head portion of each screw has a truncated conical shape across its vertical cross section, the head portion of each screw extending from a maximum circular diameter along the screw-head taper to a minimum circular diameter, the body portion of each screw having a cylindrical shape across its vertical cross section, wherein a body portion diameter of each screw is the same as the minimum circular diameter of the screw-head.

6. The apparatus of claim 1, wherein the plate has a generally trapezoidal horizontal-cross-section with a maximum length ranging from about 1 to about 3 inches; a width ranging from about 0.5 to about 1.5 inches; and a height ranging from about 0.1 to about 0.5 inches.

7. The apparatus of claim 1, wherein the head portion of the first and second screws each has threads for receiving respective first and second nuts, the first and second nuts having a larger average diameter than respective first and second annuluses.

8. The apparatus of claim 1, wherein at least the first aperture is generally rectangular across its horizontal cross section.

9. The apparatus of claim 7, wherein the head portion of the first screw has an upper first head-portion taper for engaging a first upper taper of the first annulus, and the head portion of the second screw has an upper second head-portion taper for engaging a second upper taper of the second annulus.

10. The apparatus of claim 1, wherein the external surface of the first annulus forms a general semi-circle along its vertical cross section, and the bore of the rectangular slide is configured to be engaged with the external surface of the first annulus.

11. The apparatus of claim 10, wherein the semi-circular exterior surface of the first annulus comprises a radius of about 0.1 inches to about 0.4 inches.

12. The apparatus of claim 1, wherein the external surface of the second annulus forms a general semi-circle along its vertical cross section and the second aperture is configured to be engaged with the external surface of the second annulus.

13. The apparatus of claim 12, wherein the semi-circular exterior surface of the second annulus comprises a radius of about 0.1 inches to about 0.4 inches.

\* \* \* \* \*